United States Patent [19]

Van der Knaap

[11] Patent Number: Plant 6,238

[45] Date of Patent: Aug. 2, 1988

[54] CHRYSANTHEMUM PLANT NAMED PENNY LANE

[75] Inventor: Jacques C. M. Van der Knaap, De Lier, Netherlands

[73] Assignee: Fides, Handelskwekerij, De Lier, Netherlands

[21] Appl. No.: 821,471

[22] Filed: Jan. 22, 1986

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Penny Lane particularly characterized by its light pink ray floret color and contrasting, generally dark orange disc florets: nine week response; anemone capitulum; and, excellent flower production.

1 Drawing Sheet

The present invention comprises a new and distinct cultivar of Chrysanthemum, botanically known as *Dendranthema morifolium*, Ramat., previously *Chrysanthemum morifolium*, Ramat., and referred to by the cultivar name Penny Lane.

Penny Lane is a product of a planned breeding program which had the objective of creating new Chrysanthemum cultivars with anemone capitulum with a dark colored center similar to a gerbera, nine weeks response, and the ability to produce commercially acceptable quality in year around cut mum programs. Such traits in combination were not present or needed improvement in previously available commercial cultivars.

Penny Lane was originated from a hybridization made in a controlled breeding program in De Lier, The Netherlands in 1981. The female parent was Cherub. The male parent of Penny Lane was a first generation hybrid obtained by crossing Augusta×Leimonias. Penny Lane was discovered and selected as one flowering plant within the progeny of the stated cross by Jacques C. M. Van der Knaap in June of 1982, in a controlled environment in De Lier, The Netherlands.

The first act of asexual reproduction of Penny Lane was accomplished when vegetative cuttings were taken from the initial selection in July of 1982 in a controlled environment in De Lier, The Netherlands by a technician working under formulations established and supervised by Jacques C. M. Van der Knaap. Horticultural examination of selected units initiated in November of 1982 has demonstrated that the combination of characteristics as herein disclosed for Penny Lane are firmly fixed and are retained through successive generations of asexual reproduction.

Penny Lane has not been observed under all possible environmental conditions. The phenotype may vary significantly with variations in environment such as temperature, light intensity and day length. The following observations, measurements and comparisons describe plants grown in De Lier, The Netherlands under greenhouse conditions which approximate those generally used in commercial greenhouse practice.

The following traits have been repeatedly observed and are determined to be basic characteristics of Penny Lane which, in combination, distinguish this Chrysanthemum as a new and distinct cultivar:

1. Anemone capitulum.

2. Light pink ray floret color, with the disc florets being a relatively dark orange to provide a striking contrast with the ray florets.
3. Nine week response.
4. Excellent flower production per stem.

Of the many commercial cultivars known to the present inventor, the most similar in comparison to Penny Lane is Pound About. In comparison to Pound About, Penny Lane has less vigor, a shorter response, more flowers per stem, and a darker colored center. The anemone type and ray floret color of Penny Lane are similar to those same characteristics of Pound About.

The accompanying photographic drawing shows typical inflorescence and foliage characteristics of Penny Lane, the colors being as true as reasonably possible for color photos of this type.

In the following description, color references are made to The Royal Horticultural Society Colour Chart. The color values were determined between 11:00 a.m. and 12:00 noon in November of 1982 under natural day light at De Lier, The Netherlands.

Classification:

*Botanical.*—*Dendranthema morifolium*, Ramat., cv Penny Lane.

*Commercial.*—Anemone spray.

INFLORESCENCE

A. Capitulum:

*Form.*—Flat.

*Type.*—Anemone.

*Diameter across face.*—30–55 mm.

B. Corolla of ray florets:

*Color (general tonality from a distance of three meters).*—Very pale pink to white.

*Color (upper surface).*—RHS 56D to white. The very pale pink color is hardly discernible in the color photograph.

*Color (under surface).*—RHS 155D.

C. Corolla of disc florets:

*Color (mature).*—RHS 174A in very center, surrounded by 173B, with outer ring of disc florets being 10C or even lighter at periphery.

*Color (immature).*—White to pink. Color not discernible in color photograph and difficult to specify by color value.

D. Reproductive organs:

*Androecium.*—Present in disc florets.

*Gynoecium.*—Present in both disc and ray florets.

PLANT

A. General appearance:

*Height.*—75 cm.

B. Foliage:

*Color (upper surface).*—RHS 147A.

*Color (under surface).*—RHS 147B.

*Shape.*—Lobed and serrated.

I claim:

1. A new and distinct Chrysanthemum plant named Penny Lane, as described and illustrated, and particularly characterized by its light pink ray floret color and contrasting, generally dark orange disc florets; nine week response; anemone capitulum; and, excellent flower production.

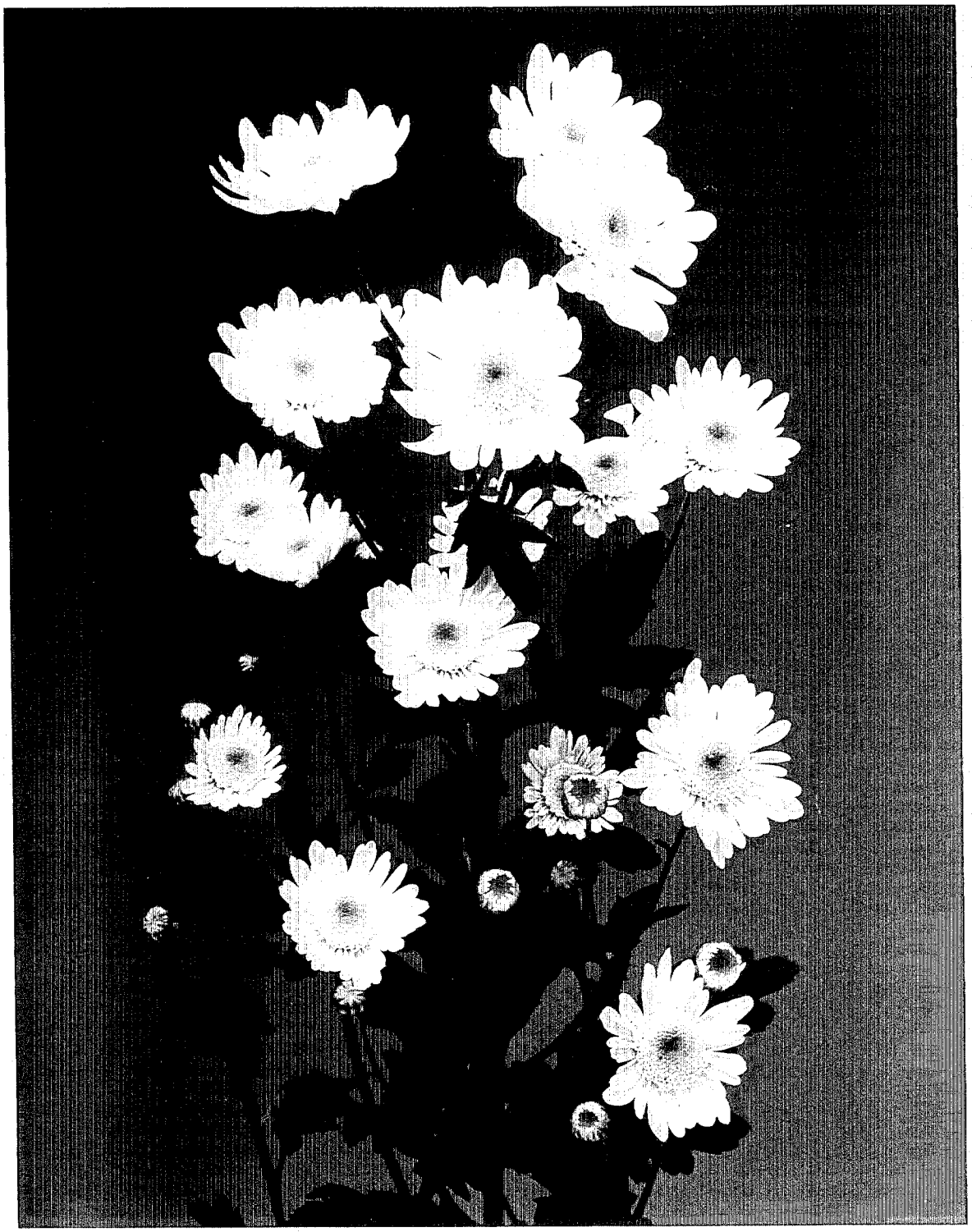

* * * * *